June 1, 1965 R. S. MOORE Plant Pat. 2,525
ROSE PLANT
Filed March 2, 1964
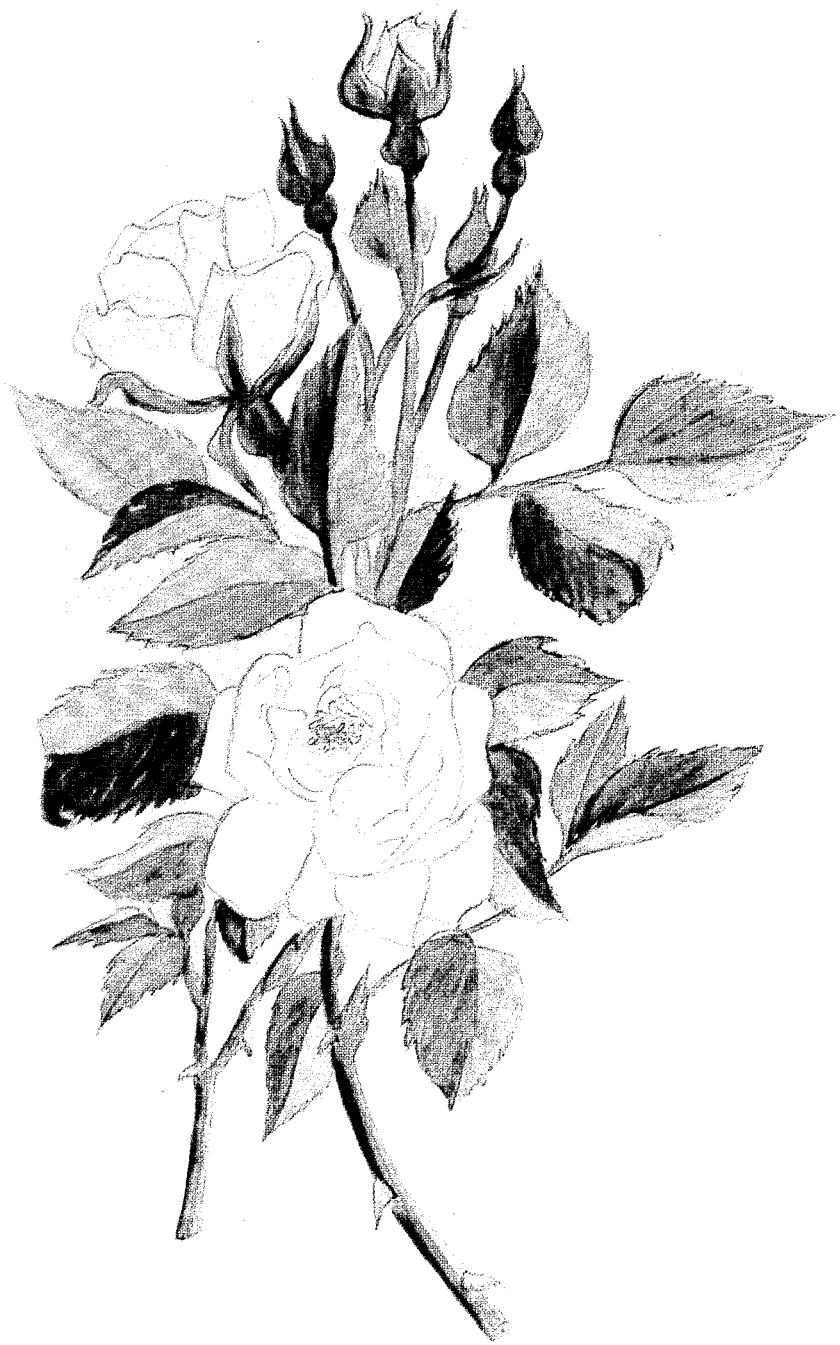
WITNESS
Jeanette Nunn Copley
INVENTOR
Ralph S. Moore
ATTORNEYS United States Patent Office Plant Pat. 2,525
Patented June 1, 1965

2,525
ROSE PLANT

Ralph S. Moore, 2519 E. Mineral King, Visalia, Calif.

Filed Mar. 2, 1964, Ser. No. 348,890
1 Claim. (Cl. Plt.—1)

The present invention relates to a new and distinct variety of hardy, upright growing, bush type rose plant of the shrub (or hedge) class; the variety being primarily characterized—as to novelty—by its medium pink to soft pink double flowers which in general effect resemble those of Pinocchio rose (Pl. Pat. 484).

The variety is further characterized by:

An abundance of bloom (a mature plant often producing more than a thousand flowers in a season); flowers borne singly but usually in loose clusters, or sprays, of from 3 to 25 or more.

A plant which is vigorous, of upright habit with glossy, medium greeen, medium small foliage; plant has a normal height of three to four feet and will grow to five feet in a hedge.

A plant which has a much branched growth habit, resembling Little Buckaroo (Pl. Pat. 1,726), only more vigorous.

A plant which grows and blooms abundantly from spring to fall, suitable for use as a flowering shrub, hedge, a garden rose and producer of flowers for cutting.

The present variety of rose plant was originated by me in my nursery located at Visalia, California, under conditions of careful control and observation, as a cross of an unnamed and unpatented seedling (*Rosa wichuraiana* × Floradora, both unpatented) as the seed parent, and Little Buckaroo (Pl. Pat. 1,726) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, bud and flower.

Referring now specifically to the new and distinct variety of shrub (or hedge) rose plant, the following is a detailed description thereof; all major color plate identifications being by reference to the British Colour Council Horticultural Colour Chart, except where common terms of color identification are employed.

Type: Hardy; vigorous, upright, bush; seedling; outdoors; shrub, hedge, pot (or tub) plant; garden decoration; cut flowers.

Class: Shrub; hedge.

Flowers:

*Continuity.*—Continuous.

*Fragrance.*—Slight.

Flowers borne: Usually in clusters of 3 to 25, on medium length, wiry stems.

Quantity of bloom: Abundant in spring and recurring more or less continually to fall.

Bud:

*Peduncle.* — Medium long; slender; erect — stiff (wiry); medium green; few greenish prickles (nearly smooth).

*Before calyx breaks.* — Size — small to medium. Form—pointed; with some foliaceous appendages on surface of bud; with foliaceous parts extending beyond tip of bud equal to one-half or more of its length.

*Color.*—Medium green.

*As calyx breaks.*—Color pink. As first petal opens: size—medium-small; form—short pointed.

*Color as first petal opens.*—Outside—pink; inside—pink.

*Opening.*—Usually opens well.

Bloom:

*Size when fully open.*—2 to 2½ inches.

*Petalage.*—Double—20 to 25 petals, arranged regularly.

*Form.*—High centered at first, with petals rolled loosely outward, later becoming cup shaped with outer petals rolled loosely outward.

Petals: Leathery (medium); satiny inside and outside. Shape: outside petals broad lanceolate; intermediate—broad lanceolate; inside—lanceolate to broad lanceolate.

Color: Newly opened flower from a plant grown in the greenhouse (December 1963), Visalia, California.

*Outside petal.* — Outside surface — Neyron Rose 623/2 with dilution of white near base; inside surface—Carmine Rose 621/2 with dilution of white at base.

*Intermediate petal.*—Outside surface—Neyron Rose 623/2 with dilution of white at base; inside surface—Carmine Rose 621/2 with dilution of white at base.

*Inner petal.*—Outside surface—Neyron Rose 623/2 with dilution of white at base; inside surface—Carmine Rose 621/2 with dilution of white at base.

General color effect:

*Newly opened flower.*—Soft medium pink with a slight coral undertone.

*Three days open.*—Same pink, slightly lighter tone but without coral undertone.

*Outdoors.*—In sunshine—flower color often begins to deepen.

Behaviour: Petals are inclined to persist for a time.

Flower longevity: Bush in garden (September 1963) 5 to 7 days. Cut flowers kept at living room temperature—3 to 5 days (September 1963).

Reproductive organs:

*Stamens.*—Medium amount; arranged regularly about pistils.

*Filaments.*—Medium length; yellow; most with anthers.

*Anthers.*—Small to medium; yellow; open mostly all at once.

*Pollen.*—Moderate to abundant; yellow.

*Pistils.*—Moderate number.

*Styles.*—Pale yellow to near white.

*Ovaries.*—All enclosed.

*Hips.*—Few to moderate number; small ovoid; orange-red; smooth; walls thin.

*Sepals.*—Permanent; medium long; spear shaped; recurved. Color—medium green (same as peduncle); sometimes darker green and tinted bronze outdoors.

*Seeds.*—Few—1 to 3 per hip. Germination, poor to average.

Foliage:

*Leaves.*—Compound of five (sometimes 7) leaflets; abundant; moderately leathery; glossy.

*Leaflets.*—Shape—lanceolate; apex acute; base round (sometimes moderately acute). Margin—serrate. Color—medium green; new growth sometimes tinted bronze. Rachis—medium strength; upper surface grooved with occasional tiny, very short, hairs (or prickles); under side sparsely to moderately thorny (thorns hook downward). Stipules—medium length; fairly broad; short length points turning out at an angle of about 45 degrees.

Growth:

*Habit.*—Bushy; upright; much branched from the base and upward.

*Growth.*—Free; vigorous. Canes—medium.

*Main stems.*—Color—dull green. Thorns—moderately thorny; long oval base; length medium to long; hooked downward. Color—brown. Prickles—none. Hairs—none.

*Branches.*—Color—medium green. Thorns—moderately thorny; medium length; slender; hooked downward; long oval base; color—brown.

*New shoots.*—Color—bright green, often tinted bronze. Thorns—moderately thorny; medium length; slender; hooked downward; long oval base; color—reddish. Prickles—usually none. Hairs—a few; usually smooth or nearly so.

The rose plant and its flowers as herein described may vary in slight detail due to climatic, soil and cultural conditions under which the variety may be grown; the present description being of the variety as grown at Visalia, California.

The following is claimed:

A new and distinct variety of rose plant of hardy, upright, much branched, bush type, as illustrated and described, charcterized by buds and flowers resembling the Pinocchio (Plant Patent 484) in size and general form but with a more high-centered flower, more pointed bud, not so many petals and more pink color; the plant being more upright than Pinocchio, resembling in its upright growth habit the variety Floradora, but being more branched with thinner more wiry branches and canes; the bush more resembling the Little Buckaroo (Plant Patent 1,726) in general growth structure but being taller, more vigorous, with larger, lighter green leaves, larger flowers; and further characterized by a plant easy to propagate from cuttings, with abundant, medium-small, glossy, medium green foliage; an abundance of bloom with flowers of cut flower quality borne several to a stem in loose clusters—often from ten to twenty or more flowers in each cluster or spray.

No references cited.

ABRAHAM G. STONE, *Primary Examiner.*